United States Patent [19]

Duthoo et al.

[11] Patent Number: 6,099,718
[45] Date of Patent: Aug. 8, 2000

[54] METHOD AND DEVICE FOR CHECKING AND CHARACTERISTICS OF A SURFACE LAYER OF A ZIRCONIUM-ALLOY ELEMENT AND USE FOR THE CHECKING OF FUEL RODS FOR A NUCLEAR REACTOR

[75] Inventors: Dominique Duthoo; Fanjas Yves, both of Romans; Alain Frichet, Mions; Michel Ladet, Seyssins, all of France

[73] Assignee: Société Franco-Belge de Fabrication de Combustible - FBFC, Courbevoie, France

[21] Appl. No.: 09/029,995

[22] PCT Filed: Sep. 17, 1996

[86] PCT No.: PCT/FR96/01445

§ 371 Date: May 6, 1999

§ 102(e) Date: May 6, 1999

[87] PCT Pub. No.: WO97/12224

PCT Pub. Date: Apr. 3, 1997

[30] Foreign Application Priority Data

Sep. 27, 1995 [FR] France .................... 95 11332

[51] Int. Cl.[7] .................... G01N 27/26

[52] U.S. Cl. .................... 205/791; 204/404; 204/434; 205/775; 205/776.5; 324/71.1; 324/71.2; 376/249; 376/305

[58] Field of Search .................... 204/404, 434; 205/775, 776.5, 791, 791.5; 324/71.1, 71.2

[56] References Cited

U.S. PATENT DOCUMENTS

| | | | |
|---|---|---|---|
| 3,166,485 | 1/1965 | Lloyd | 204/404 |
| 4,425,193 | 1/1984 | Taylor | 204/404 |
| 4,806,849 | 2/1989 | Kihira et al. | 204/404 |
| 4,831,324 | 5/1989 | Asakura et al. | 204/404 |
| 5,246,560 | 9/1993 | Nekoksa et al. | 204/404 |
| 5,323,429 | 6/1994 | Roarty et al. | 376/249 |
| 5,404,104 | 4/1995 | Rivola et al. | 205/791 |
| 5,493,904 | 2/1996 | Shih et al. | 204/434 |

*Primary Examiner*—T. Tung
*Attorney, Agent, or Firm*—Pollock, Vande Sande & Amernick

[57] ABSTRACT

A sinusoidal voltage is appied to a zirconium alloy clad fuel rod. The current is measured and the impedance is determined to provide a check for the compactness and adhesion of an oxide surface layer on the fuel rod.

8 Claims, 2 Drawing Sheets

METHOD AND DEVICE FOR CHECKING AND CHARACTERISTICS OF A SURFACE LAYER OF A ZIRCONIUM-ALLOY ELEMENT AND USE FOR THE CHECKING OF FUEL RODS FOR A NUCLEAR REACTOR

FIELD OF THE INVENTION

The invention relates to a method for checking the characteristics of a surface layer consisting especially of oxide on a zirconium-alloy element of a fuel assembly for a nuclear reactor.

BACKGROUND OF THE INVENTION

Fuel assemblies for a nuclear reactor and, in particular, fuel assemblies for a water-cooled nuclear reactor, include, inside a framework, fuel rods which are held together in the form of a bundle in which the rods are mutually parallel.

The fuel rods generally consist of a tube made of an alloy which is a weak absorber of neutrons, such as a zirconium alloy, in which pellets of nuclear fuel are stacked. After the tubes have been filled with the fuel pellets, they are closed at their ends by plugs which are welded to the tube making up the clad of the rod. The fuel-assembly framework itself consists of elements which are mostly made of an alloy which in a weak absorber of neutrons, such as a zirconium alloy. Zirconium and its alloys are passivatable metals, i.e., metals on whose surface a passivation layer, consisting of a very thin oxide, forms naturally, this layer protecting the metal from aggressive external environments.

In the case of fuel rod clads or of other elements of a fuel assembly made of zirconium alloy, this passivation layer establishes in particular the conditions under which ions and electrons are exchanged between the metal of the fuel-assembly elements and the very-high-temperature and high-pressure water for cooling the reactor, while the nuclear reactor is operating. This passivation layer changes during use.

The characteristics of the oxide layer, with regard to the effectiveness of the protection, depend to a large extent on the initial conditions under which this layer was formed at the surface of the zirconium-alloy element.

In general, corrosion inside a nuclear reactor cooled by pressurized water produces, on a zirconium-alloy substrate consisting of sound metal, at least during the first phases of corrosion, a black, shiny, adherent and protective zirconia layer. In contrast, on a metal which does not have the required metallurgical characteristics or which has been contaminated during a manufacturing phase such as welding, corrosion develops by forming a white, non-adherent and non-protective zirconia layer.

It is therefore necessary to verify, by suitable tests, that the zirconium-alloy substrate exhibits satisfactory properties after manufacture of the fuel-assembly element.

In the case of a fuel rod, the ends of which are closed by welded plugs, it is necessary to verify whether the weld zone is completely free of contaminating products. To this end, a 360° three-day corrosion test is performed on the rod in an autoclave, and then the appearance of the passivated surface layer in the region of the plug welds is checked. In the case of a satisfactory contamination-free weld, the passivation oxide layer is uniformly black. The presence of contamination in the region of the weld is manifested by quite extensive white traces or by a greyish coloration.

Such an autoclave corrosion test has drawbacks in the context of industrial-scale manufacture of fuel rods.

The reason for this is that the duration of the corrosion test, taking into account the time for the temperature of the autoclave to rise and fall, is five days, during which the fuel-rod production unit continues production without having the assurance that the welding unit is operating properly. The corrective measures necessary in the case of contamination cannot therefore be taken immediately. This drawback may lead to products being scrapped or significant numbers of products having to be repaired. Furthermore, the units produced may be put into circulation after checking only at the end of the test, which affects the manufacturing flexibility and increases the quantity of semi-finished products in the course of manufacture. Furthermore, the corrosion test is a destructive test which can only be carried out on a small number of specimens per work station. The autoclaves used for the tests are permanently sequestered.

The result of the corrosion test is a purely qualitative all-or-nothing result which does not make it possible to determine the deviation of the production output with respect to the desired standard.

Finally, there is no reliable and quick method making it possible to verify that the welding chamber is correctly purged and that the shielding gas which it contains is correct.

SUMMARY OF THE INVENTION

The object of the invention is to propose a method for checking the characteristics of a surface layer, consisting especially of oxide, of a zirconium-alloy element of a fuel assembly for a nuclear reactor, which is quick and non-destructive and which makes it possible to obtain a quantitative result without requiring the use of complex test equipment. In particular, the method must make it possible to check an oxide layer on a zirconium-alloy element, such as, for example, a fuel-rod cladding tube, and especially to compare the level of quality of the weld of the fuel-rod plug quantitatively with respect to defined criteria.

To this end, a sinusoidal voltage V is applied in a measurement zone on the zirconium-alloy element, the intensity I of a sinusoidal current flowing in the measurement zone is measured, the impedance $Z=V/I$ of the measurement zone on the element is determined and the impedance obtained is compared with at least one reference value in order to deduce therefrom the characteristics of the surface layer.

BRIEF DESCRIPTION OF THE DRAWINGS

In order for the invention to be clearly understood, an embodiment of the method according to the invention will now be described, by way of example with reference to the appended drawings, in the case of the checking of the surface passivation layer formed after a welding operation in the region of the weld zone of the fuel-rod plugs for a pressurized-water nuclear reactor.

DESCRIPTION OF PREFERRED EMBODIMENT

Figure 1:
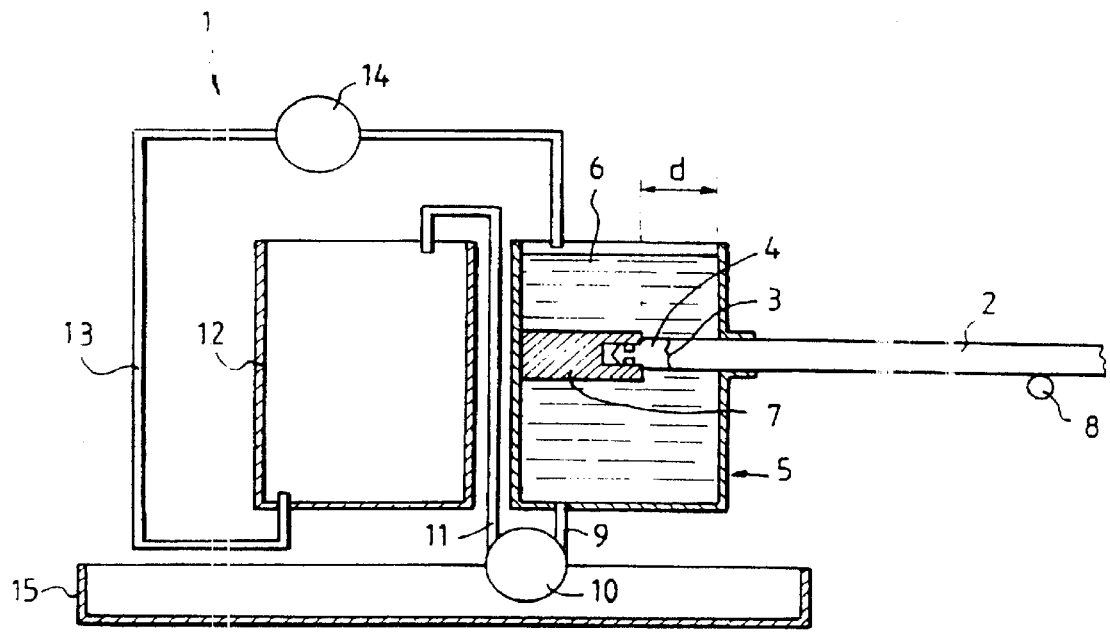
FIG. 1 is a schematic elevation view of an installation for checking the welded end zone of fuel rods.
Figure 2:
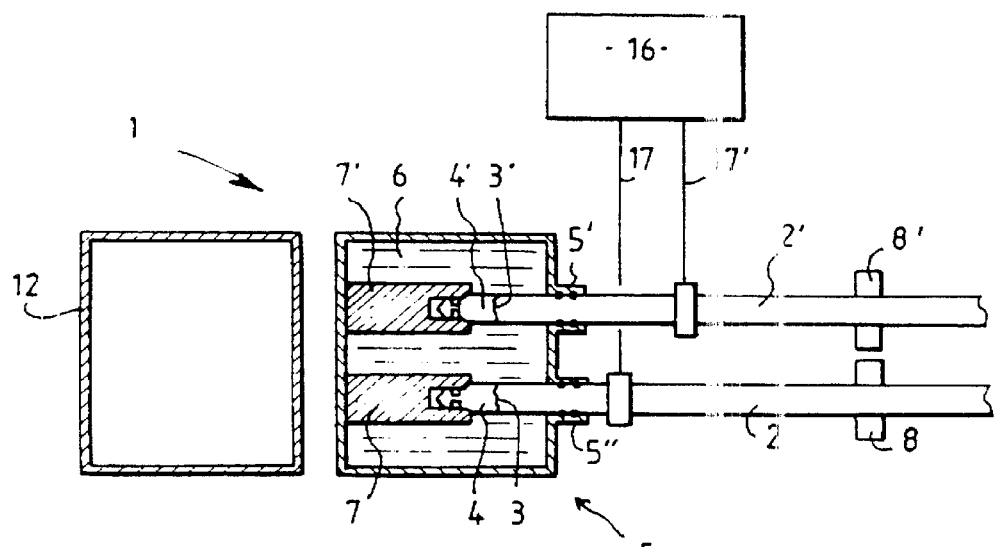
FIG. 2 is a plan view in the direction 2 of FIG. 1.

FIGS. 1 and 2 show a checking device 1, making it possible to check the oxide layer formed on the clad of fuel rods 2, 2', in the region of the weld zone 3, 3' of a plug 4, 4' for closing off one end.

The checking installation 1 makes it possible either to check two rods 2, 2' simultaneously or to check one fuel rod 2 in a comparative manner with respect to a standard 2' consisting of a reference fuel rod or a similar element.

The fuel rods 2 or 2' have a tubular zirconium-alloy clad inside which pellets of fuel material are stacked. The clad of the rod is closed at both its ends by plugs 4, which are forcibly engaged inside the end part of the clad and are fixed by a weld line 3. The external surface of the zirconium-alloy clad of the rod is covered with an oxide layer which protects the metal of the clad.

In an operating nuclear reactor, the oxide layer thickens and becomes more substantial during the initial phases of residence of the fuel element in the primary part of the nuclear reactor, the protective layer taking the form of a black shiny zirconia layer which provides effective protection of the clad during operation of the reactor as well as during shutdown periods when the fuel assemblies are handled and any repairs carried out.

During manufacture, should the external surface of the clad suffer certain types of damage, for example should the operation of welding the plugs lead to the presence of contaminants on the external surface of the clad, the oxide layer is liable to become porous or to be discontinuous, so that the rod is no longer satisfactorily protected.

The checking installation shown in FIGS. 1 and 2 makes it possible to determine, by means of an impedance measurement, whether the oxide layer formed on the end part of the rod having the plug exhibits satisfactory characteristics. In particular, the checking method makes it possible to determine if the oxide layer is perfectly compact and adherent to the external surface of the clad and that it exhibits no defects due, for example, to traces of contamination in the weld zone 3.

The checking installation 1 includes a test vessel 5 which contains an electrolyte 6 and is provided with means for penetration by and for support of the end parts of two fuel rods 2, 2'.

The means for penetration by the rods 2, 2' consist of two nozzles 5', 5" which are fixed to the wall of the vessel 5 at openings penetrating the wall of the vessel, inside each of which is arranged a set of seals and electrical insulation means.

The devices for support 7, 7' of the ends of the rods 2, 2' are fixed to the wall of the vessel 5 lying opposite the wall to which the nozzles 5', 5", lying respectively on the extension of the supports 7, 7', are fixed. Each of the supports 7, 7' includes an opening for engagement of the end part of a plug 4, 4' of a fuel rod 2 or 2'.

The devices for support of the rods also include, outside the test vessel 5, two rollers 8, 8', on each of which the clad of a rod 2 or 2' rests when the end part of the rod comprising the plug 4 or 4' is engaged in the test vessel 5.

The bottom of the test vessel 5 is penetrated by a drain pipe 9 which is connected to a pump 10 whose delivery part is connected to a pipe 11 extending into the upper part of an electrolyte storage tank 12.

The bottom of the electrolyte storage tank 12 is penetrated by a feed pipe 13 into which is inserted a charging pump 14. The feed pipe 13 runs into the upper part of the test vessel 5. A liquid-catching pan 15 is placed under the test vessel 5, the tank 12 and the drain pump 10.

A description will now be given, with reference to FIGS. 1 and 2, of an operation of checking of the oxide layer in the end part of a fuel rod 2.

Initially, the test vessel 5 is empty of electrolyte and the ends of a rod 2 to be checked are introduced through the nozzle 5" so that the plug 4 of the fuel rod 2 engages in the opening in the support 7. The seals arranged inside the nozzle 5" are compressed by the rod 2 so that they can provide sealing with respect to the liquid electrolyte around the rod 2. In addition, the clad of the rod is electrically isolated from the vessel. The rod 2 rests on a support roller 8 made of electrically insulating material.

Likewise, a second fuel rod 2' to be checked is engaged through the nozzle 5" and into the opening in the second support 7'. The second rod 2' rests on a second roller 8' made of insulating material, outside the test vessel 5.

The second rod 2' may be a rod which is to be checked at the same time as the rod 2 is checked, or a standard rod having a layer whose characteristics are fully known.

The charging pump 14 and the feed pipe 13 are used to fill the test vessel 5 with liquid electrolyte 6. The clad of the rods 2 and 2' is then immersed in the liquid electrolyte to a length d, the weld zone 3 or 3' of the fuel-rod plug being immersed in the liquid electrolyte 6.

The checking installation includes an impedance measurement device 16, in the form of a module consisting of a sinusoidal electrical current source and of means for measuring and recording the sinusoidal voltage delivered by the current source, and a device for measuring and recording the intensity of the current generated by the electrical current source.

Each of the terminals of the sinusoidal alternating electrical current source 16 is connected to a respective conductor 17 or 17'. Each of the electrical conductors 17 and 17' is fastened at its end to a fixing and contacting clamp which may be engaged on and fixed to a part of the fuel rod 2 or 2' lying outside the test vessel 5.

The conductor 17 is connected to the external surface of the clad of the rod 2 while the conductor 17' is connected to the external surface of the clad of the rod 2'.

The sinusoidal electrical current source makes it possible for a current to be made to flow through the oxide layer of the clad of the rod 2, immersed in the electrolyte 6, through the electrolyte 6 and through the oxide layer of the clad of the rod 2'.

The impedance Z corresponding to the ratio of the voltage V to the intensity I of the current is measured by a measuring and recording unit of the module 16.

This impedance is representative of the state of oxidation of the end parts of the clads of the rods 2 and 2'.

The voltage V of the sinusoidal alternating current is of the form $V=V_0 \cos \omega t$. This voltage is that fixed by the electrical current source.

The intensity I which is measured and recorded by the module 16 has the form $I=I_0 \cos(wt-\phi)$.

The rated voltage V is limited to a low value in order to avoid any action by the current on the clad of the rod dipped into the electrolyte. $V_0$ may be fixed to a value of 10 millivolts, for example.

The module 16 makes it possible to determine and record the complex impedance $Z^*=V/I=(V_0/I_0)e^{j\phi}$.

The complex impedance is therefore characterized by the impedance modulus $V_0/I_0$ and by the phase shift $\phi$.

Impedances obtained from the measured intensity of the electrical current are compared with reference values which make it possible to determine the state of the oxide layer on the clad of the rod or rods and in particular the state of the oxide layer in the region of the rod's weld 3 or 3'.

In fact, the oxide layer at the surface of the zirconium-alloy clad behaves in an essentially capacitive manner. The impedance measurement therefore makes it possible to determine the capacitance of the oxide layer which, to a first approximation, may be expressed by the formula $|Z|=1/\omega C$, in which:

Z is the impedance of the oxide layer,

C is the capacitance of the oxide layer, $\omega=2\pi f$, f being the frequency of the current.

The electrical current source has a variable frequency so that the measurement conditions can be adjusted.

Should the impedance be high, i.e., if the capacitance is low, it is possible to deduce from this, because there is little ion and electron exchange through the layer, that a protective oxide is present. Conversely, if the impedance is lower and therefore the capacitance higher, it is possible to deduce from this that there is a decrease in the protective nature of the oxide layer.

However, it is necessary to determine the equivalent electrical circuit, of the not purely capacitive type, most representative of the oxide layer.

By comparing the impedance values of an obtained capacitance with reference values, it is possible to obtain, directly as output from the control module 16, an evaluation of the characteristics of the protective oxide layer with regard to its uniformity and its adherence.

In particular, it is possible to determine, in a precise manner, whether the welding of the plugs has been carried out satisfactorily, and especially that it has not been contaminated.

Figure 3:
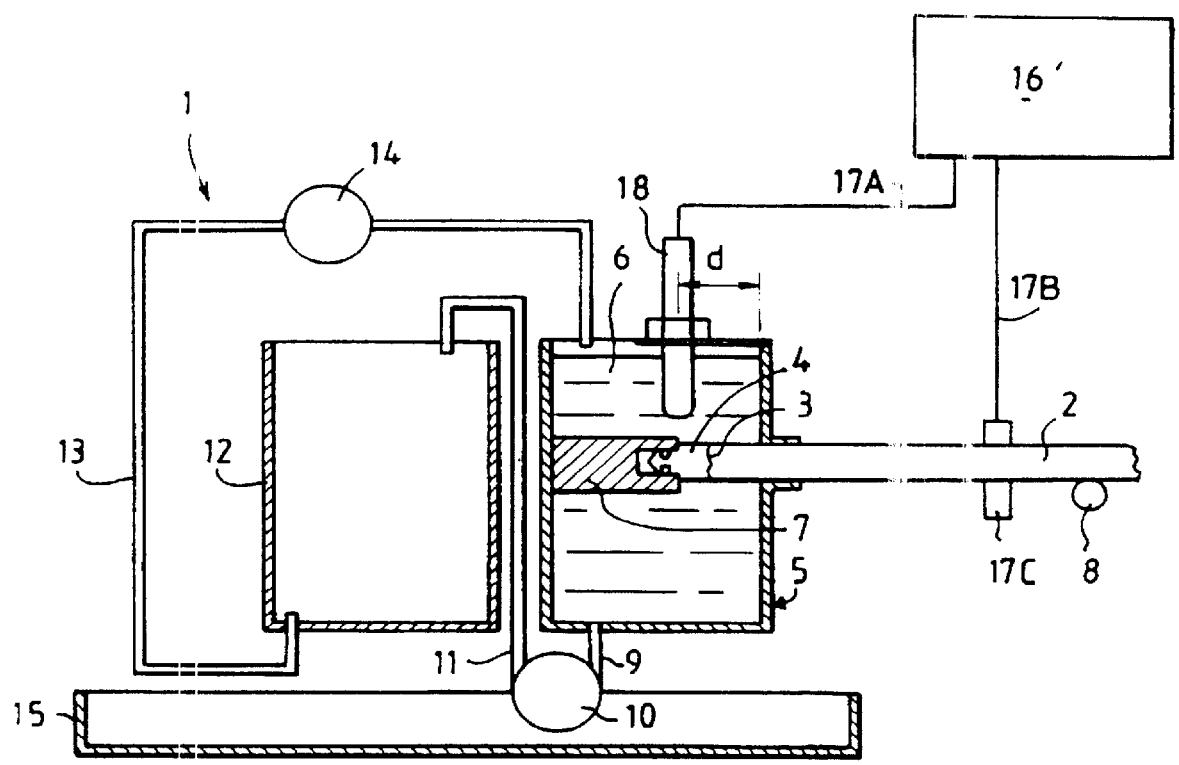
FIG. 3 is a view, similar to FIG. 1, of an alternative embodiment of the checking installation.

FIG. 3 shows an alternative embodiment of the measurement installation according to the invention.

The elements which correspond in FIGS. 1 and 3 bear the same reference numbers. The measurement installation shown in FIG. 3 enables an impedance measurement to be made on a single fuel rod 2 introduced into and supported in the test vessel 5 in the same way as the rods shown in FIGS. 1 and 2.

An electrode 18 introduced via the upper part of the vessel 5 dips into the liquid electrolyte 6 contained in the vessel. The electrode 18 is connected via an electrical conductor 17a to one of the terminals of a sinusoidal alternating current source of an impedance-measuring device 16' in the form of a module which includes the alternating current source and means for measuring and recording the sinusoidal voltage delivered by the source and the intensity of the current generated by the electrical source. The second terminal of the alternating current source is electrically connected by means of an electrical conductor 17b and by a clamp 17c to part of the clad of the rod 2 lying outside the test vessel 5. The impedance measurement is carried out as described previously and makes it possible to check the characteristics of the surface layer of the rod, as previously. The electrical current delivered by the electrode 18 flows through the electrolyte, reaching the end of the rod, and then through the end zone of the rod 2.

The device according to the alternative embodiment in FIG. 3 makes it possible to check fuel rods individually and, in particular, to check the weld zone of the plug of each of the rods introduced into the test vessel 5.

It is quite obvious that it is possible to use a test vessel having several points for the positionning of several fuel rods which may be checked in succession. All that is required is to move the clamp 17c successively to the position for clamping the rod on which the check is to be made. The electrode is made of material which resists attack by the electrolyte 6.

The method according to the invention makes it possible to carry out a rapid measurement (in a few minutes), without destroying or impairing the clad of the fuel rod, because the chemical composition and concentration of the electrolyte, as well as the measurement voltage used, are chosen so as not to impair the oxide layer or the zirconium-alloy substrate. Ultimately, the measurement is very sensitive, so that levels of contamination not detectable by the standard prior art test method may be detected.

Furthermore, the check results in a quantitative measurement of the impedance which enables the various levels of contamination of the oxide layer resulting from the welding operation to be accurately distinguished.

The measurement method also makes it possible to obtain information about the structure of the oxide layer and, in particular, to know whether the oxide layer is porous or compact. Because of the speed of the measurement, it is possible to react immediately, should the check show that there is a drift from the chosen reference values. Because the check is non-destructive, it may be carried out on the products coming from manufacture and not on controls chosen by sampling.

Finally, because of its sensitivity, the checking method according to the invention makes it possible to predict how the operation of the fuel-rod production line, in particular the plug-welding unit, may change.

It is possible to use a test vessel which does not have nozzles for penetration by the fuel rods. In this case, the fuel rods are introduced into the vessel via its top, which is open, and dipped into the electrolyte liquid over a certain length, below the upper level of the electrolyte liquid in the vessel.

It is possible to make impedance measurements on the surface oxide layer of a fuel rod in a different way from that which has been described, with or without the use of an electrolyte. The measurements may be made on a single fuel rod or on several rods.

The method according to the invention is also applicable in the case of fuel-assembly elements made of a passivatable alloy such as a zirconium alloy, other than a fuel rod. The method according to the invention may be applied, for example, to the guide tubes or to the grids making up the framework of the fuel assembly, which are generally made of zirconium alloy, the check being made using a suitable device.

We claim:

1. A method for checking compactness and adhesion of a surface layer consisting of oxide covering an external surface of a fuel rod for a nuclear reactor upon completion of manufacture of said fuel rod, said fuel rod having a tubular zirconium alloy clad containing pellets of fuel material and closed at both ends by plugs made of zirconium alloy welded on said clad, checking of the surface layer being performed in at least one measurement zone covering a weld of a plug to said clad in an end part of said fuel rod, said method comprising the steps of:

(a) applying a sinusoidal voltage V to a measurement zone of said surface layer;

(b) measuring an intensity I of a sinusoidal measurement current flowing in said measurement zone;

(c) determining an impedance Z=V/I of said measurement zone of said surface layer; and (d) comparing the impedance obtained with at least one reference value in order to determine whether compactness and adhesion of said surface layer are satisfactory.

2. The method according to claim 1, wherein said impedance Z is substantially equal in absolute value to $1/\omega C$, where C is the capacitance of the surface oxide layer and $\omega=2\pi f$, f being the frequency of the measurement current, said method comprising determining the presence of a compact and protective layer if C has a low value and determining the presence of a non-protective porous layer if C has a high value.

3. The method according to claim 1, comprising applying a measurement current to said measurement zone of said surface layer by means of an electrolyte.

4. The method according to claim 3, comprising passing said measurement current between two fuel rods, an end part of each fuel rod being dipped in said electrolyte so that said measurement current flows through a first fuel rod to an end of said first fuel rod, then through said electrolyte to an end part of a second fuel rod and then through a part of said second fuel rod.

5. The method according to claim 3, comprising passing said measurement current between an electrode dipped in said electrolyte and a fuel rod having an end part dipped in said electrolyte so that the current flows through said electrode, through said electrolyte to the end part of said fuel rod.

6. A device for checking compactness and adhesion of a surface layer consisting of oxide covering an external surface of a fuel rod for a nuclear reactor upon completion of manufacture of said fuel rod, said fuel rod having a tubular zirconium alloy clad containing pellets of fuel material and closed at both ends by plugs made of zirconium alloy welded on said clad, checking of the surface layer being performed in at least one measurement zone covering a weld of a plug to the clad in an end part of said fuel rod, said device comprising:

(a) a test vessel;

(b) means for feeding said test vessel with liquid electrolyte;

(c) said fuel rod having an end part immersed in said liquid electrolyte;

(d) an electrical supply module delivering a sinusoidal measurement voltage to the end part of said fuel rod immersed in said electrolyte, through an electrical connection means;

(e) an impedance measuring module for determining the impedance from the sinusoidal voltage and a measurement current flowing in the end part of said fuel rod; and (f) means for comparing the measured impedance to at least a reference value and for evaluating the compactness and adhesion of the surface layer from a result of the comparison.

7. A device according to claim 6, wherein said test vessel includes means supporting said fuel rod and a second fuel rod in an immersed position of their end parts in the electrolyte and means of connection between said electrical supply module and each of said fuel rods.

8. A device according to claim 6, further including an electrode dipped in said electrolyte and means of electrical connection between said electrical supply module and said electrode and said fuel rod.

* * * * *

UNITED STATES PATENT AND TRADEMARK OFFICE
CERTIFICATE OF CORRECTION

PATENT NO. :  6,099,718
DATED      :  August 8, 2000
INVENTOR(S) : Dominique Duthoo et al.

It is certified that error appears in the above-identified patent and that said Letters Patent is hereby corrected as shown below:

Title page
Under [75] inventors, replace "Fanjas Yves" with --Yves Fanjas--

Signed and Sealed this

Seventeenth Day of April, 2001

Attest:

NICHOLAS P. GODICI

*Attesting Officer*    *Acting Director of the United States Patent and Trademark Office*